Figures 1, 2:
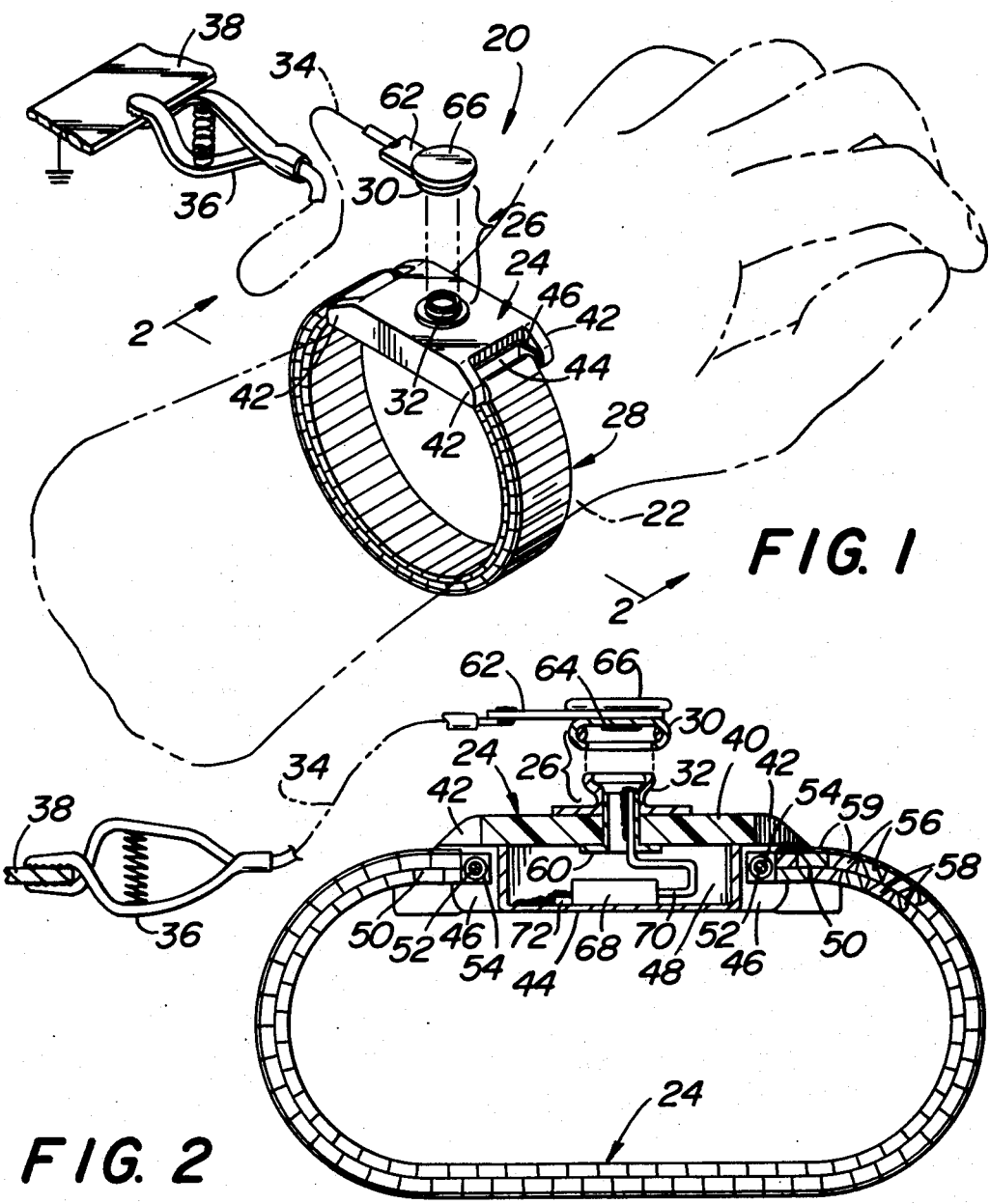

United States Patent [19]

Vandermark

[11] Patent Number: 4,459,633
[45] Date of Patent: Jul. 10, 1984

[54] DEVICE FOR DRAINING STATIC ELECTRICITY

[75] Inventor: Harold F. Vandermark, Blue Bell, Pa.

[73] Assignee: Nu-Concept Computer Systems, Inc., Colmar, Pa.

[21] Appl. No.: 303,432

[22] Filed: Sep. 18, 1981

[51] Int. Cl.³ .............................................. H05F 3/02
[52] U.S. Cl. ..................................... 361/220; 361/212
[58] Field of Search ...................... 361/212, 220, 223; 174/5.53; 128/381, 384, 783, 802, 908

[56] References Cited

U.S. PATENT DOCUMENTS

| | | | |
|---|---|---|---|
| 2,586,747 | 2/1952 | Van Atta | 361/223 |
| 3,015,754 | 1/1962 | Legge | 361/223 |
| 3,359,456 | 12/1967 | De Woskin | 317/1 |
| 3,379,932 | 4/1968 | Legge | 317/2 |
| 3,596,134 | 7/1971 | Burke | 317/2 B |
| 3,745,412 | 7/1973 | Ruff | 361/220 |
| 3,857,397 | 12/1974 | Brosseau | 128/384 |
| 4,104,695 | 8/1978 | Hollis et al. | 361/220 |
| 4,373,175 | 2/1983 | Mykkanen | 361/220 |

*Primary Examiner*—Reinhard J. Eisenzopf
*Attorney, Agent, or Firm*—Caesar, Rivise, Bernstein & Cohen, Ltd.

[57] ABSTRACT

A device for grounding static electricity from a person comprising a case and connected band to be worn on the limb of the person. The device includes an electrically conductive inner surface and an electrically insulative outer surface. A releasably securable connector is provided between a ground connection and the conductive inner surface of the device. A resistor is connected between the connector and the inner surface of the device and is located within the case.

5 Claims, 2 Drawing Figures

U.S. Patent  Jul. 10, 1984  4,459,633

DEVICE FOR DRAINING STATIC ELECTRICITY

This invention relates generally to devices for grounding static electricity and more particularly to devices to be worn by persons to drain static electricity to ground.

Fragile electronic components, such as integrated circuits, and other components frequently mounted on circuit boards are readily susceptible and damaged due to static electricity. The problem occurs when a difference in potential exists between personnel handling the electronic component and the component itself. At the time this occurs, if the person is charged with high voltage static electricity and if the electrical component is susceptible to damage from such high voltage, it may be completely or partially damaged, even though very little current passes through the device.

Precautions are taken in the industry to prevent this problem. Among the techniques utilized are the use of a grounded conductive mat on the work table surface for the printed circuit board to rest upon. A conductive wrist strap is provided about the wrist of the individual and in contact with the skin and is connected to ground or to the grounded mat via a strap or wire between the strap and ground.

Another method of grounding the individual is through the use of a boot made of a conductive material worn over the shoes and contacting the skin surface of the ankle. A conductive floor mat is connected to the ground and to the work table surface.

The wearing of a conductive wrist strap to effectuate grounding of static electricity, as carried out in the prior art, has presented substantial drawbacks. In this regard it will be appreciated that a conductive wrist strap connected to ground presents a shock or electrocution hazard to the individual in the event that some conductive piece or part of the strap or ground wire come in contact with a high voltage/current carrying conductor. In an attempt to eliminate the electrocution or shock hazard, prior art conductive band static drain devices frequently make use of a resistor installed in the ground wire.

In some prior art devices, the resistor is placed in series in the ground wire adjacent the ground clip. In such an arrangement, if the ground wire should be severed or the insulation broken and the exposed conductor contacted by a high voltage conductor, the current flow bypasses the resistor thus exposing the wearer to shock or electrocution. In other prior art devices, the resistor is in series in the ground wire but immediately adjacent the connector on the conductive band. While this embodiment may eliminate the shock hazard, the resistor or its connection to the ground wire is exposed to mechanical damage resulting from frequent connections and disconnections of the connector or flexing of the conductor at the resistor connection point. If the resistor is broken or if the connection to the resistor is broken, an open circuit results, thereby negating the grounding function of the device.

Some other prior art devices have used non-conductive straps including a snap, button or similar type of connection which is riveted through the band so that direct metal contact is made with the skin surface in order to provide the required ground to skin connection. This technique also suffers from drawbacks in that when the snap, button or connector is unsnapped, the exposed conductive snap provides a conductive path in the band to the skin. Accordingly, if a high voltage/current carrying conductor should contact the exposed snap electrocution or shock could result.

Example of prior art devices for grounding persons to dissipate static electricity are shown in the following U.S. Pat. Nos. 3,359,456 (DeWoskin), 3,379,932 (Legge), 3,596,134 (Burke), 3,745,412 (Ruff), 3,857,397 (Brosseau), and 4,104,695 (Hollis et al).

It is a general object of the instant invention to provide a device which overcomes the disadvantages of static art grounding devices.

It is a further object of the instant invention to provide a grounding device for personnel which does not present a shock or electrocution hazard when worn.

It is a further object of the instant invention to provide a static drain device which is simple in construction, attractive, and can be readily put on and taken off.

It is a further object of the instant invention to provide a wrist worn static dissipating device including releasably securable connector means for enabling the wearer to be readily disconnected from ground and without exposing the person to a shock or electrocution hazard.

These and other objects of the instant invention are achieved by providing a device for draining static electricity from a person comprising a case, connector means and band means secured to the case for encircling the portion of the limb of a person. The band comprises an inner surfae and an outer surface. The outer surface is electrically insulative. The case includes an electrically insulative outer surface. The device also includes an electrically conductive inner surface. The inner surface of the case is arranged for engagement and electrical contact with a portion of the skin of the wearer. The case includes resistance means located therein. The connector means comprises first and second electrically conductive connector elements. The first connector element is mounted on the case. The second connector element is arranged for releasable securement and electrical contact with the first connecting element. The second connecting element is arranged to be grounded. The resistance means is electrically interconnected between the first connector element and the inner surface.

Other objects and many of the attendant advantages of this invention will be readily appreciated as the same becomes better understood by reference to the following detailed description when considered in connection with the accompanying drawing wherein:

FIG. 1 is a perspective view of a static draining device constructed in accordance with the instant invention and shown in the normal operative position, but with portion of the connector means of the device shown separated for clarity; and FIG. 2 is an enlarged sectional view taken along line 2—2 of FIG. 1.

Referring now in greater detail to the various figures of the drawing wherein like reference numerals refer to like parts, there is shown at 20 in FIG. 1 a static dissipating device constructed in accordance with the instant invention. The device 20 is arranged to be worn about the wrist 22 of a person, such as a person working on static voltage sensitive electronic components. The device 20 basically comprises a case 24, connector means 26 and a band or strap 28.

The band 28 will be described in detail later, suffice for now to state that it is connected to the case in the manner similar to a conventional wristwatch band and is arranged to be worn about the wrist 22. The band and case each include an electrically conductive inner surface, to be described in detail later, which makes contact with the skin. The connector 26 provides the means for electrically interconnecting the inner surface of the band and the case to ground. To that end, the connector means 26 includes a female snap element 30 and a male snap element 32. The male snap element 32 is mounted on the case and is in electrical continuity with the conductive, skin-engaging portions of the case and band. The female snap element includes an electrically conductive portion which is electrically connected to an electrically insulated conductor wire 34. The conductor wire terminates at its end in a conventional electrically conductive spring clip 36 arranged to be secured to a grounded member 38. Thus, when the clip 36 is grounded and the snap element 30 secured to snap element 32, an electrically conductive path is provided between ground and the skin of the person, via the clip 36, conductor 34, snap element 30, snap element 32 and the inner surface of the case 24 and the band 28.

In order to obviate the potential electric shock hazard to the wearer by contact with a high voltage current carrying conductor, the entire exposed outer surface of the device 20 of the instant invention is electrically insulative, i.e., dielectric.

The case includes resistance means, to be described later, which is interconnected between the snap element 32 and the electrically conductive inner surface of the device to prevent an shock or electrocution hazard should the snap connector elements be disconnected and contact made by element 32 to a high voltage/current conductor.

Referring now to FIG. 2 the details of the device 22 will be described.

The case 24 basically comprises the top 40 of generally rectangular configuration and having two pair of parallel extending ears 42. Each ear extends from the corner of the case top parallel to the longitudinal dimension of the case top. The ears 42 serve as means for connecting the band 28 to the case 24, as will be described hereinafter. The case 24 also includes a case bottom 44. The bottom is a rectangular, tray-shaped member having two pair of ears 46 extending from the corners thereof. The ends 46 also extend parallel to the longitudinal direction of the case bottom 44 and are spaced apart by a sufficient distance so as to fit snuggly between the ears 42 of the case top. case bottom is disposed directly under the top so that the top seals or closes an interior cavity 48 and with the bottom of the case back engaging the wearer's skin at the wrist within the case.

In a preferred embodiment of the invention, the case top 40 is formed of an electrically insulative material, such as a nylon type material sold under the tradename ZYTEL by E. I. DuPont de Nemours & Co, Inc., while the case bottom 44 is formed of an electrically conductive material, such as stainless steel.

The band 28 is an elongated, strap-like expansion assembly which includes an opposed pair of ends 50. Each end 50 is arranged to be secured between the opposed ears 46 of the case bottom and the associated ears 42 of the case top in a manner similar to the method of connection between a conventional watch case and watch band. To that end, a roll-type pin 52 extends through a connecting link 54 at each end of the band. The pin 52 passes through aligned openings (not shown) in the ears 46 and 42 at each end of the case to secure each end of the band to an associated side of the case.

The band 28 shown in FIG. 2 is formed of plural interconnected links to enable the band to expand. As noted heretofore, the outer surface of the band 28 is formed of an electrically insulative material while the inner surface is formed of an electrically conductive material. To that end, in accordance with the embodiment shown in FIG. 2, band 28 comprises a plurality of interconnected, outer link members 56 and a plurality of interconnected inner link members 58. The links 56 and 58 are formed of an electrically conductive material, e.g., stainless steel, with the links of each layer being pivotally connected together in a conventional manner, like expansion watch bands. Accordingly, when the device 20 is on the wrist 22 as shown in FIG. 1, the electrically conductive links 58 engage the surface of the skin underlying the band 28. Each end link 54 and roll pin 52 are also formed of an electrically conductive material, e.g., stainless steel. Accordingly, electrical continuity exists all along the inner surface of the case back and inner surface of the band.

In accordance a primary aspect of this invention the outer surface of the band, i.e., the top links 56, are coated or laminated with an electrically insulative material, e.g., a polyethylene terephthalate based plastic.

The connector means 26, as noted heretofore, comprises male and female snap connector elements 32 and 30, respectively. Element 32 is a conventional male snap element formed of an electrically conductive material, e.g., steel, and is mounted in the central portion of the case top 40 and projects upward normally therefrom. The element 32 is secured in place, via a hollow rivet 60, extending through the case top. The female connector element 30 is arranged to mate with the male element 32 and also is of conventional construction and formed of an electrically conductive material, e.g., steel. The conductor 34 is an elongated, electrically conductive cable or wire of conventional construction and connected to a tang 62 formed of an electrically conductive material. The tang is permanently secured to the snap element 30, via an electrically conductive rivet or button 64. The button 64 includes an enlarged cap 66 formed of an insulative or conductive material and located over the snap element 30.

The resistance means located within the case 24 is a conventional resistor 68. The resistor 68 is connected in electrical series between the male snap element 32 and the case bottom 44. To that end, one lead 70 of the resistor is secured, such as by soldering, etc., to the interior of rivet 60 and is thus in electrical contact with the snap 32. The other lead 72 of the resistor 68 is secured, such as by soldering, to the case bottom 44. The resistor is selected to have sufficiently high resistance to provide isolation between the snap 32 and case bottom and the band's inner surface to prevent a shock hazard in the event that snap element 30 is exposed by the disconnection of snap 32 therefrom or in the event that a high voltage conductor comes into contact with an exposed portion of the ground wire, i.e., a portion of the ground wire where the insulation is broken or eroded, etc.

By locating the resistor in the case, it is immediately adjacent to the wearer and thus will always be interposed between the person wearing the device and any high voltage conductor, irrespective of where the conductor makes contact with the device's ground wire or connector, thus ensuring against shock or electrocution. Moreover, the location of the resistor within the case protects the resistor from mechanical damage, which has characterized prior art grounding devices. Furtherstill, the solder connections of the resistor's leads to the case bottom and the male snap resist mechanical damage since such connections are internal and not subject to flexing or movement. Accordingly, the chances of a break in the electrical continuity of the ground device is minimized.

As will be appreciated from the foregoing, the device of the instant invention is simple in construction, attractive in appearance, can be readily put on or taken off, yet provides a safe and effective means for grounding persons to dissipate static electricity. Moreover, by virtue of the ready disconnectability of the snap elements 30 and 32 personnel wearing the device can be free to move about without requiring the disconnection of the spring clip 36 from a grounded element. Further still the use of the resistance means located within the case ensures that a shock hazard does not result in the event that a person does disconnect the snap means 26 and the snap 32 engages a high voltage/current carrying conductor or in the event that some portion of the ground wire becomes exposed to contact by a high voltage conductor. Moreover, the mechanical protection of the resistor, as provided by its location within the case, ensures against a break in the electrical continuity of the ground path which would be caused by mechanical failure of the resistor or its connections in the circuit path. Finally, in the event that a break occurs in the ground conductor, all that is required to render the device operative is to connect any wire between ground and the male snap 32 by wrapping one end of the wire about the snap and attaching the other end of the wire to some grounded body.

It must be pointed out at this juncture that while the device is shown as consisting of outer links 58 formed of a electrically conductive material coated with an insultative coating, it is clear that the outer links can themselves be formed of an electrically insultative material.

It must also be pointed out at this juncture that while the preferred embodiment the band 28 includes an electrically conductive inner surface in engagement with the skin at the wrist or any other portion about which the band is disposed, such an arrangement is not exclusive. In this regard, the band need not include an electrically conductive inner surface so long as the bottom of the case 24 is electrically conductive. Conversely, the bottom of the case may be formed of an electrically insulative material so long as the inner surface of the band is electrically conductive and the resistor is connected between the snap and the electrically conductive inner surface of the band. In such alternative embodiments, the contact between either the back of the case and the skin of the wearer or the inner surface of the band and the skin of the wearer is sufficient to provide a static electricity dissipating ground path. Thus, it is contemplated that the band 28 can be formed of any material such as leather, cloth, plastic, etc.

Finally, it must be understood that while the device 20 is shown for disposition about the wrist of a person, it is clear that the device can be provided to encircle any suitable portion of a persons body, e.g., the ankle etc.

Without further elaboration the foregoing will so fully illustrate my invention that others may, by applying current or future knowledge, readily adapt the same for use under various conditions of service.

What is claimed as the invention is:

1. A device for draining static electricity from a person to ground while preventing a shock hazard by contact of said device with a high voltage/current carrying conductor and comprising a case, connector means and band means secured to said case, said case including an inner portion and an outer portion, said outer portion having an outer surface and said inner portion being electrically conductive and arranged for electrical contact with a portion of the body of said person, said band means being arranged for encircling a portion of the body of a person and comprising an inner and outer surface, said inner surface of said band being arranged for direct contact with said body portion of said person, said case including electrical resistance means located therein, said connector means comprising a first connector element and a second connector element, each of said connector elements being electrically conductive, said second connector element arranged to be grounded, said first connector element being mounted on said case, said second connector element being arranged for releasable securement and electrical contact with said first connector element, said resistance means being electrically interconnected between said first connector element and said electrically conductive inner portion of said case, said outer surface of said band and said outer surface of said case being electrically insulative, both of said outer surfaces being out of electrical and direct physical contact with the inner surface of said band, said conductive inner portion of said case and said body portion, whereupon when said device is in position encircling said body portion the insulative outer surfaces deter electrical contact by said high voltage/current carrying conductor with said body portion.

2. The device of claim 1 wherein said inner surface of said band is electrically conductive.

3. The device of claim 2 wherein said device also comprises an electrically insulative outer surface covering both of said connector elements when they are secured together.

4. The device of claim 1 wherein said band is expandable.

5. The device of claim 4 wherein said band comprises plural interconnected links.

* * * * *